United States Patent [19]

Castrejon

[11] Patent Number: 4,656,668
[45] Date of Patent: Apr. 14, 1987

[54] EYE PROTECTOR

[76] Inventor: Diane A. Castrejon, 1321 S. Finley Rd., Lombard, Ill. 60148

[21] Appl. No.: 880,109

[22] Filed: Jun. 30, 1986

Related U.S. Application Data

[63] Continuation of Ser. No. 757,244, Jul. 22, 1985.

[51] Int. Cl.$^4$ .............................................. A61F 9/00
[52] U.S. Cl. ............................................ 2/15; 2/426
[58] Field of Search ................. 2/15, 12, 13, 426, 446; 128/132 R

[56] References Cited

U.S. PATENT DOCUMENTS

| | | | |
|---|---|---|---|
| 207,624 | 9/1878 | Ricketts | 2/12 |
| 589,307 | 8/1897 | Seffer | 2/15 |
| 900,444 | 10/1908 | Stickle | 2/13 |
| 2,243,982 | 6/1941 | Seeley | 2/12 |
| 2,671,898 | 3/1954 | Wade | 2/15 |
| 2,769,308 | 11/1956 | Krasno | 2/12 |
| 3,020,552 | 2/1962 | Coon | 2/15 |
| 3,619,815 | 12/1971 | Toroner, Jr. | 2/12 |
| 3,780,379 | 12/1973 | Kampman | 2/15 |
| 4,162,542 | 7/1979 | Frank | 2/15 |
| 4,411,263 | 10/1983 | Cook | 2/15 |
| 4,502,476 | 3/1985 | Weft | 2/15 |

FOREIGN PATENT DOCUMENTS

685935  7/1930  France ..................... 2/12

*Primary Examiner*—Werner H. Schroeder
*Assistant Examiner*—Mary A. Ellis
*Attorney, Agent, or Firm*—Wood, Dalton, Phillips, Mason & Rowe

[57] ABSTRACT

A device for protecting the eyes of a user. The eye protector includes a pair of substantially light impervious eye cups formed of an absorbent flexible material and adapted to fit over the closed eyes of the user. Each of the eye cups is sized and shaped to substantially entirely cover the region defined by one of the orbital openings in the skull of the user. The material is sufficiently absorbent to retain water and sufficiently flexible to conform to the closed eyes of the user. The eye protector also includes a bridge band adapted to fit over the nose bridge of the user. The bridge band is formed of an elastic material capable of expanding and contracting to vary the spacing between the eye cups to accommodate the difference in spacing between the orbital openings in the skulls of different users. The bridge band is permanently secured to the eye cups. The eye protector further includes a head band adapted to fit around the head of the user. The head band is formed of an elastic material capable of expanding and contracting to retain the eye cups in position over the closed eyes of the user while accommodating the differences in head sizes among different users. The head band is permanently secured to the eye cups. With these features, the eye protector is adapted to protect the eyes of the user from light, sand, heat, dirt, sun and the like.

7 Claims, 5 Drawing Figures

EYE PROTECTOR

This is a continuation of co-pending application Ser. No. 757,244, filed on July 22, 1985.

BACKGROUND OF THE INVENTION

The present invention relates to a device for protecting the eyes of the user and, more particularly, to an eye protector of unique construction adapted for universal applicability.

It is generally recognized that many people are quite concerned with their overall appearance. This is evident from a wide range of commonly observed and experienced phenomena including the rapid growth in the number of health clubs, the attention given to overall diet, media focus on sports and physical fitness related activities, diet and health spas directed to vacationers, resorts in tropical and subtropical regions, and tanning salons. Of present interest, many persons have a significant interest in safely obtaining a deep tan.

As a result, there has been a significant growth in skin care products. These have ranged from tanning lotions and enhancers, to sun screens having various degrees of effectiveness in blocking the sun's rays, to after tanning moisturizer creams. More recently, some attention has been given to providing protection for the eyes of sunbathers.

In particular, many sunbathers have a strong tendency to lie in the sun for lengthy periods with their eyes closed. However, this exposes their eyelids to the harmful, burning rays of the sun and, since it is inadvisable to place lotions and sunscreens in and closely about the eyes, the eyelids can easily be burned. Moreover, this problem is aggravated by the fact that the eyelids are for the most part sensitive skin regions.

In addition to the problem of burning the eyelids, the sun's rays are known to dry the skin to an unhealthy degree. This problem is partially alleviated for areas of the skin covered with tanning lotions or sunscreens but, again, it is usually advised that such materials be avoided in and around the region of the eyes. For this reason, there has been no known way to keep the eyelids moistened during periods of exposing the remainder of the body to the sun's rays.

A further problem of significant concern has been the potential danger from sand in the eyes. It is well known to those who spend time at the beach that the wind can cause drifting sand to enter the region in and around the eyes which is most irritating and potentially damaging to the eyes. As a result, it has remained for someone to provide a means for protecting the eyes from exposure to sand at the beach.

The present invention is directed to overcoming the above stated problems and accomplishing the stated objectives.

SUMMARY OF THE INVENTION

Accordingly, the present invention is directed to a device for protecting the eyes of a user. The eye protector includes a pair of substantially light impervious eye cups formed of an absorbent flexible material and adapted to fit over the closed eyes of the user. Each of the eye cups is sized and shaped to substantially entirely cover the region defined by one of the orbital openings in the skull of the user. The material is sufficiently absorbent to retain water and sufficiently flexible to conform to the closed eyes of the user.

The eye protector also includes a bridge band adapted to fit over the nose bridge of the user. The bridge band is formed of an elastic material capable of expanding and contracting to vary the spacing between the eye cups to accommodate the difference in spacing between the orbital openings in the skulls of different users. The bridge band is permanently secured to the eye cups.

The eye protector further includes a head band adapted to fit around the head of the user. The head band is formed of an elastic material capable of expanding and contracting to retain the eye cups in position over the closed eyes of the user while accommodating the differences in head sizes among different users. The head band is permanently secured to the eye cups.

With these features, the eye protector is adapted to protect the eyes of the user from light, sand, heat, dirt, sun and the like.

In a preferred embodiment, the absorbent flexible material is a soft cellular foam to avoid skin irritations on the eyelids of the user. It is also advantageous for the eye cups each to have an outer periphery of generally oval shape to closely conform to the shape of the orbital openings in the skull of the user and a contour of generally cup shape to closely conform to the shape of the closed eyes of the user. Additionally, the eye protector preferably includes means for permanently securing the bridge band and the head band to the eye cups.

More specifically, the securing means preferably includes an end portion of the bridge band and the head band extending through the soft cellular foam of each of the eye cups on opposite sides thereof. In the preferred embodiment, it also includes a separate enlargement such as a compressible bead-like member permanently associated with each of the extending end portions.

Other objects, advantages and features will become apparent from the following specification taken in conjunction with the accompanying drawings.

DETAILED DESCRIPTION OF THE PREFERRED EMBODIMENT

Figure 1:
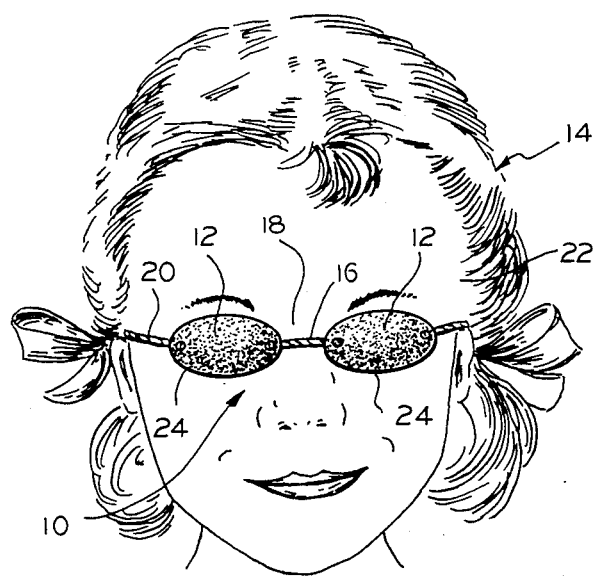
FIG. 1 is a front elevational view of a device for protecting the eyes of a user in accordance with the present invention.
Figure 2:
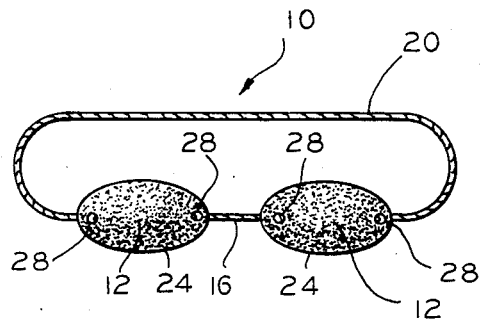
FIG. 2 is a front elevational view of the eye protector of FIG. 1.
Figure 3:
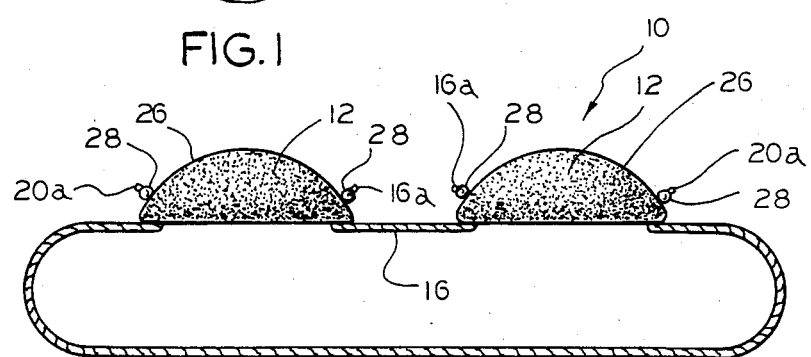
FIG. 3 is a top plan view of the eye protector of FIG. 1.
Figure 4:
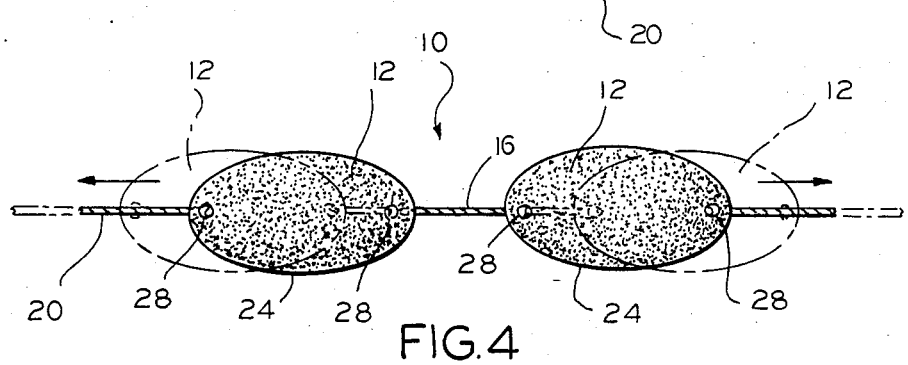
FIG. 4 is a front elevational view similar to FIG. 2 illustrating the adjustability of the eye protector.

An exemplary embodiment of an eye protector according to the invention is illustrated in FIGS. 1 through 5. The eye protector 10 includes a pair of substantially light impervious eye cups 12 formed of an absorbent flexible material and adapted to fit over the closed eyes of a user 14. Each of the eye cups 12 is sized and shaped to substantially entirely cover the region defined by one of the orbital openings in the skull of the user 14. The material is sufficiently absorbent to retain water and sufficiently flexible to conform to the closed eyes of the user 14.

The eye protector 10 also includes a bridge band 16 adapted to fit over the nose bridge 18 of the user 14. The bridge band 16 is formed of an elastic material capable of expanding and contracting to vary the spacing between the eye cups 12 (see FIG. 4) to accommodate the difference in spacing between the orbital openings in the skulls of different users. The bridge band 16 is permanently secured to the eye cups 12.

The eye protector 10 further includes a head band 20 adapted to fit around the head 22 of the user 14. The head band 20 is formed of an elastic material capable of expanding and contracting to retain the eye cups 12 in position over the closed eyes of the user 14 while accommodating the differences in head sizes among different users. The head band 20 is permanently secured to the eye cups 12.

With these features, the eye protector 10 is adapted to protect the eyes of the user from light, sand, heat, dirt, sun and the like.

Figure 5:
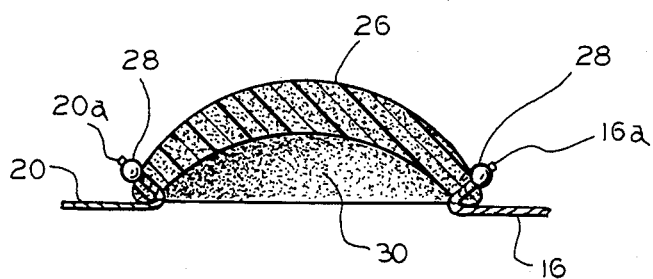
FIG. 5 is a cross-sectional view of the eye protector of FIG. 1.

Referring to FIG. 1, the eye cups 12 each have an outer periphery 24 of generally oval shape to closely conform to the shape of the orbital openings in the skull of the user 14. In addition, the absorbent flexible material of the eye cups 12 is preferably a soft cellular foam such as polyeurethene to avoid skin irritations on the eyelids of the user 14. Referring to FIG. 5, the eye cups 12 each have a contoured surface 26 of generally cup shape to closely conform to the shape of the closed eyes of the user 14.

As will be appreciated, the eye protector 10 includes means for permanently securing the bridge band 16 and the head band 20 to the eye cups 12. The securing means includes an end portion 16a of the bridge band 16 and an end portion 20a of the head band 20 extending through the soft cellular foam of each of the eye cups 12 on opposite sides thereof, and further includes a separate enlargement 28 permanently associated with each of the extending end portions 16a and 20a. As shown, the separate enlargements 28 each preferably comprise a compressible bead-like member.

As shown in FIG. 5, the eye cups 12 are preferably molded to provide the generally cup shape contoured surface 26. It will also be appreciated that the eye cups 12 can be formed of substantially uniform thickness, or of contoured thickness as shown. Moreover, the eye cups 12 are preferably formed of a single thickness of soft cellular foam.

As will be appreciated, the soft cellular foam may allow some light to pass through the eye cups 12. The degree to which this occurs can be controlled by selecting the material and density of material which in one successful embodiment was formed of eighty (80) pore clickable polyeurethene foam. If desired, a double thickness of soft cellular foam can be used for the eye cups 12.

In addition, the eye cups 12 can be formed such that the outer contoured surface 26 is a light color to reflect the sun's rays. This will promote the light impervious nature of the eye cups 12 as well as helping to keep the eyes cool during use of the eye protector 10. Moreover, the eye cups 12 can be formed such that the inner contoured surface 30 is a dark color to shield the eyes from bright sunlight.

As shown in the drawings, the bridge band 16 is sufficiently thin to avoid leaving a significant tan line on the nose bridge 18 of the user 14. It will also be noted from FIG. 4 that the bridge band 16 is sufficiently elastic to permit the spacing between the eye cups 12 to be automatically varied to accommodate the difference in spacing between the orbital openings in the skulls of different users. Further, the head band 20 is sufficiently thin to avoid leaving a significant tan line on each side of the head 22 of the user 14.

As previously mentioned, the bridge band 16 and the head band 20, which may advantageously be metallic covered elastic bands, are permanently secured to the eye cups 12. This is accomplished while still being able to utilize soft cellular foam as the absorbent flexible material for the eye cups 12 by means of the compressible bead-like members 28 which grip the ends 16a and 20a extending through the eye cups 12, thereby preventing the ends 16a and 20a from pulling through the soft cellular foam. In addition, the compressible bead-like members 28 not only prevent the ends 16a and 20a from pulling through the eye cups 12, but also give an aesthetically pleasing, fashionable appearance to the eye protector 10.

As previously suggested, the absorbent flexible material of the eye cups 12 is utilized for several reasons. First, the material avoids skin irritations on the eyelids of the user. Second, the material is substantially light impervious. Third, the material is substantially sand impervious. Fourth, the material is cool on the closed eyes of the user. In this respect, the absorbent flexible material accommodates air circulation around the eyes and the eye cups 12 can be soaked in water for further cooling.

With regarding to cooling the eyes of the user, this can be particularly critical for contact lens wearers. It is especially important to keep the sun out of the eyes and keep the eyes cool, particularly for those using extended wear contact lenses, in order to avoid drying out the eyes and thus causing severe irritation. Moreover, for contact lens wearers, it is important to ensure that sand and dirt do not enter the eyes at any time.

As will be appreciated, the eye protector 10 is particularly well suited for use in many locales. This includes health clubs, beaches, resorts, cruises, and anywhere it is important to keep light, sand, heat, dirt, sun and the like from the eyes of the user, and to keep the user's eyes cool. With the unique arrangement of the present invention, an eye protector having uniform applicability has been provided.

While in the foregoing there has been set forth a preferred embodiment of the invention, it is to be understood that the invention is only to be limited by the spirit and scope of the appended claims.

I claim:
1. An eye protector, comprising:
  a pair of substantially light impervious eye cups formed entirely of an absorbent flexible material and adapted to fit over the closed eyes of a user, said absorbent flexible material comprising a soft foam-like material for each of said eye cups sized and shaped to substantially entirely cover the region defined by one of the orbital openings in the skull of the user and having a soft contoured surface of generally cup shape extending to a soft outer periphery and closely conforming to the shape of the closed eyes of the user, said soft foam-like material being sufficiently absorbent to retain water while accommodating air circulation around the eyes of the user and sufficiently flexible to conform to the closed eyes of the user;
  a bridge band adapted to fit over the nose bridge of the user, said bridge band being formed of an elastic material capable of expanding and contracting to vary the spacing between said eye cups to accommodate the difference in spacing between said eye cups so as to accommodate the difference in spacing between the orbital openings in the skulls of different users, said bridge band being permanently secured to said eye cups; and a head band adapted to fit around the head of the user, said head band being entirely separate from said bridge band and being formed of an elastic material capable of expanding and contracting to retain said eye cups in position over the closed eyes of the user while accommodating the differences in head sizes among different users, said head band being permanently secured to said eye cups;

said bridge band and said head band each having a pair of end portions, one of said end portions of each of said bridge band and head band being secured to opposite sides of one of said eye cups and the other of said end portions of each of said bridge band and head band being secured to opposite sides of the other of said eye cups such that said bridge band and head band are only secured to said eye cups at locations corresponding to opposite sides of the orbital openings in the skull of the user remote from said cup shaped contoured surface, said bridge band and said head band extering forces only on said outer peripheries of said eye cups.

2. The eye protector as defined by claim 1 wherein said absorbent flexible material is a soft cellular foam to accommodate air circulation around the eyes of the user.

3. The eye protector as defined by claim 1 wherein said outer peripheries of said eye cups are generally oval shaped to closely conform to the shape of the orbital openings in the skull of the user.

4. The eye protector as defined by claim 1 wherein said bridge band is sufficiently thin to substantially promote tanning of the entire nose bridge of the user.

5. The eye protector as defined by claim 1 wherein said head band is sufficiently thin to substantially promote tanning of the entire sides of the head of the user.

6. The eye protector as defined by claim 2 including means for permanently securing said bridge band and said head band to said eye cups, said securing means including an end portion of said bridge band and said head band extending through said soft cellular foam of each of said eye cups on opposite sides thereof, said securing means further including a separate enlargement permanently associated with each of said extending end portions.

7. The eye protector as defined by claim 6 wherein said separate enlargements each comprise a compressible bead-like member.

* * * * *